United States Patent
Li et al.

(10) Patent No.: US 10,980,468 B2
(45) Date of Patent: Apr. 20, 2021

(54) VERTIGO DIAGNOSIS AND TREATMENT SYSTEM

(71) Applicants: EYE & ENT HOSPITAL OF FUDAN UNIVERSITY, Shanghai (CN); SHENZHEN SECOND PEOPLE'S HOSPITAL, Shenzhen (CN); SHANGHAI ZEHNIT MEDICAL TECHNOLOGY CO., LTD., Shanghai (CN)

(72) Inventors: Huawei Li, Shanghai (CN); Guohui Nie, Shenzhen (CN); Yinhong Qu, Shanghai (CN)

(73) Assignees: EYE & ENT HOSPITAL OF FUDAN UNIVERSITY, Shanghai (CN); SHENZHEN SECOND PEOPLE'S HOSPITAL, Shenzhen (CN); SHANGHAI ZEHNIT MEDICAL TECHNOLOGY CO., LTD., Shanghai (CN)

(*) Notice: Subject to any disclaimer, the term of this patent is extended or adjusted under 35 U.S.C. 154(b) by 0 days.

(21) Appl. No.: 16/795,880

(22) Filed: Feb. 20, 2020

(65) Prior Publication Data

US 2020/0187844 A1 Jun. 18, 2020

Related U.S. Application Data

(63) Continuation of application No. PCT/CN2018/101190, filed on Aug. 17, 2018.

(30) Foreign Application Priority Data

Aug. 21, 2017 (CN) .......................... 201710720068.0

(51) Int. Cl.
*A61B 5/00* (2006.01)
*A61B 5/11* (2006.01)
*A47C 3/18* (2006.01)

(52) U.S. Cl.
CPC .............. *A61B 5/4023* (2013.01); *A61B 5/11* (2013.01); *A61B 5/4836* (2013.01); *A61B 5/70* (2013.01);

(Continued)

(58) Field of Classification Search
CPC ....... A61B 5/4023; A61B 5/4863; A61B 5/11; A61B 3/113; A61B 5/0496; A61B 5/6814;

(Continued)

(56) References Cited

U.S. PATENT DOCUMENTS 6,800,062 B2 * 10/2004 Epley ...................... A61B 5/11
600/558
8,066,651 B2 * 11/2011 Vitton .................... A61H 1/001
601/24

(Continued)

FOREIGN PATENT DOCUMENTS

CN 101779948 B 7/2012
CN 104146684 A 11/2014
(Continued)

OTHER PUBLICATIONS

First Office Action in counterpart Chinese Application No. 201710720068.0, dated Dec. 29, 2018.
(Continued)

*Primary Examiner* — May A Abouelela
(74) *Attorney, Agent, or Firm* — Westbridge IP LLC

(57) ABSTRACT

Disclosed is a vertigo diagnosis and treatment system including a frame, a revolution device, a rotation device and a seat, the frame comprising a primary frame and a secondary frame arranged oppositely. The revolution device includes a power mechanism and a slewing frame. The slewing frame is arranged between the primary frame and the secondary frame. The primary frame and the secondary (Continued)

frame provide slewing support for the slewing frame. The rotation device includes a power mechanism and a seat rotating frame. The vertigo diagnosis and treatment system further includes a seat biasing mechanism. Under the combined action of the revolution device and the rotation device, the vertigo diagnosis and treatment system according to the present invention can realize three-dimensional free rotation and hovering in any position, thus achieving vertigo diagnosis and treatment.

19 Claims, 4 Drawing Sheets

(52) U.S. Cl.
CPC .............. *A47C 3/18* (2013.01); *A61B 2560/02* (2013.01); *A61B 2560/04* (2013.01)

(58) Field of Classification Search
CPC ......... A61H 1/001; G06F 3/013; G06F 3/012; A47C 3/18
USPC ............... 600/300, 301, 558, 559, 587, 595; 601/23, 24, 25, 86; 297/326
See application file for complete search history.

(56) References Cited

U.S. PATENT DOCUMENTS

| | | | |
|---|---|---|---|
| 8,702,631 B2* | 4/2014 | Maher | G09B 9/10 601/26 |
| 9,183,756 B2* | 11/2015 | Maher | A61H 1/001 |
| 2003/0116166 A1 | 6/2003 | Anthony | |
| 2007/0106184 A1* | 5/2007 | Vitton | A61B 5/702 601/86 |
| 2007/0161875 A1* | 7/2007 | Epley | A61B 5/11 600/301 |
| 2007/0167886 A1* | 7/2007 | Epley | A61B 5/702 601/86 |
| 2011/0028872 A1* | 2/2011 | Kevin | A61B 5/11 601/86 |
| 2012/0118299 A1* | 5/2012 | Miller | A61F 5/3792 128/870 |
| 2016/0106614 A1* | 4/2016 | Kim | A61G 5/04 297/326 |
| 2016/0213149 A1* | 7/2016 | Budagher | A61H 1/001 |
| 2016/0213545 A1* | 7/2016 | Budagher | A61G 15/02 |
| 2016/0303484 A1* | 10/2016 | Masutti | G09B 9/12 |
| 2017/0312160 A1* | 11/2017 | Patel | A61H 1/001 |

FOREIGN PATENT DOCUMENTS

| | | |
|---|---|---|
| CN | 104510446 A | 4/2015 |
| CN | 105193389 A | 12/2015 |
| CN | 106821595 A | 6/2017 |
| CN | 107440689 A | 12/2017 |
| CN | 107468213 A | 12/2017 |
| CN | 304495072 S | 2/2018 |
| WO | 02091982 A1 | 11/2002 |

OTHER PUBLICATIONS

International Search Report and Written Opinion in corresponding PCT Application No. PCT/CN2018/101190, dated Nov. 1, 2018.

* cited by examiner

Stimulate the left utricle     Stimulate the bilateral utricle     Stimulate the right utricle

VERTIGO DIAGNOSIS AND TREATMENT SYSTEM

CROSS-REFERENCE TO RELATED APPLICATIONS

This application is a continuation of International application No. PCT/CN2018/101190 filed on Aug. 17, 2018, which claims the benefit and priority of Chinese patent application No. 201710720068.0 filed on Aug. 21, 2017. Both of these applications are incorporated herein in their entireties by reference.

TECHNICAL FIELD

The present invention relates to the field of medical devices, and in particular, to a vertigo diagnosis and treatment system.

BACKGROUND

The vestibular system contains two sensory organs, semicircular canal and otolith organs. The semicircular canal senses angular acceleration and provides central eye movement reflex for gaze stabilization when the head is turned, and the otolith organs include the utricle and the saccule, which can sense linear acceleration and provide vestibular spinal cord reflection for position stabilization. Otolith organs, as sensors of the combined forces of gravity and inertial force, can sense the spatial orientation. Otoliths are normally attached to the otolith membrane. Otoliths in the otolith organs may fall off from their original positions due to head trauma or localized structural degradation in the old age, and swim in the fluid called inner lymph in the inner ear. When the human head position changes, their semicircular canals also change position. The floating otoliths move with the flow of fluid, which stimulates semicircular canal hair cells, causing the body to experience severe vertigo. Vertigo is generally short, ranging from a few seconds to a few minutes, which can be aggravated or relieved periodically. The duration of the disease varies. This condition is called otolithiasis and also known as benign paroxysmal positional vertigo (BPPV), which refers to the transient paroxysmal vertigo and nystagmus that occurs when the head moves rapidly to a specific head position.

Benign paroxysmal positional vertigo is a clinically common peripheral vestibular disease that can be seen in all ages and is more common in the elderly. The disease is self-limiting. The most commonly affected semicircular canal is the posterior semicircular canal (accounting for 80% to 90%), followed by the lateral semicircular canal (accounting for 10%), and the least affected is the superior semicircular canal (accounting for 2%). When the posture of the human body changes, different semicircular canals receive different stimuli. The corresponding semicircular canals can be stimulated through accelerating or decelerating the rotation of different semicircular canals in different planes. Therefore, vertigo can be treated through stimulation to the corresponding semicircular canals by accelerating or decelerating the rotation of different semicircular canals in different planes and directions.

In addition, the current series of vestibular function tests are performed by vestibulo-ocular reflex (VOR) induced by stimulation of the terminal organs of the vestibule of the inner ear. Semicircular canal VOR function tests have been developed for a long time and are widely used, while otolith organ VOR function tests have been developed lately. There has been a lack of corresponding laboratory test technology for a long time.

Chinese patent application 201510621775.5 discloses a gear type vertigo diagnosis and treatment system, which realizes multi-dimensional positioning and rotation. Chinese patent application 200910000200.6 also discloses a similar body position rotating device. However, there has been no report on a device that can simultaneously perform vertigo diagnosis and treatment as well as evaluation of otolith organ functions, especially a device that separately evaluates otolith organ functions of the left and right ears through unilateral centrifugal testing.

SUMMARY

The present invention provides for the first time a vertigo diagnosis and treatment system, comprising a frame, a revolution device, a rotation device and a seat, the frame comprising a primary frame and a secondary frame arranged oppositely, the revolution device comprising a power mechanism and a slewing frame, the slewing frame being arranged between the primary frame and the secondary frame, the primary frame and the secondary frame providing slewing support for the slewing frame, the rotation device comprising a power mechanism and a seat rotating frame, the seat being arranged on the seat rotating frame, the seat rotating frame being arranged inside the slewing frame, the slewing frame providing rotation support for the seat rotating frame, and the axis of rotation of the seat rotating frame and the axis of slewing of the slewing frame being perpendicular to each other.

The vertigo diagnosis and treatment system according to the present invention can realize three-dimensional free rotation and hovering at any position under the combined action of the revolution device and the rotation device, thus achieving the effects of semicircular canal VOR function detection and otolith reset.

The vertigo diagnosis and treatment system may further include a seat biasing mechanism which includes support bases and a horizontal guide rail arranged on the support bases, the support bases being fixed on the seat rotating frame, and the seat being slidably connected with the horizontal guide rail. Under the action of the seat biasing mechanism, a person under test can be shifted to left and right with respect to the axis of rotation, so as to achieve the purpose of separately evaluating the functions of the left and right otolith organs.

DETAILED DESCRIPTION OF THE EMBODIMENTS

Figure 1:
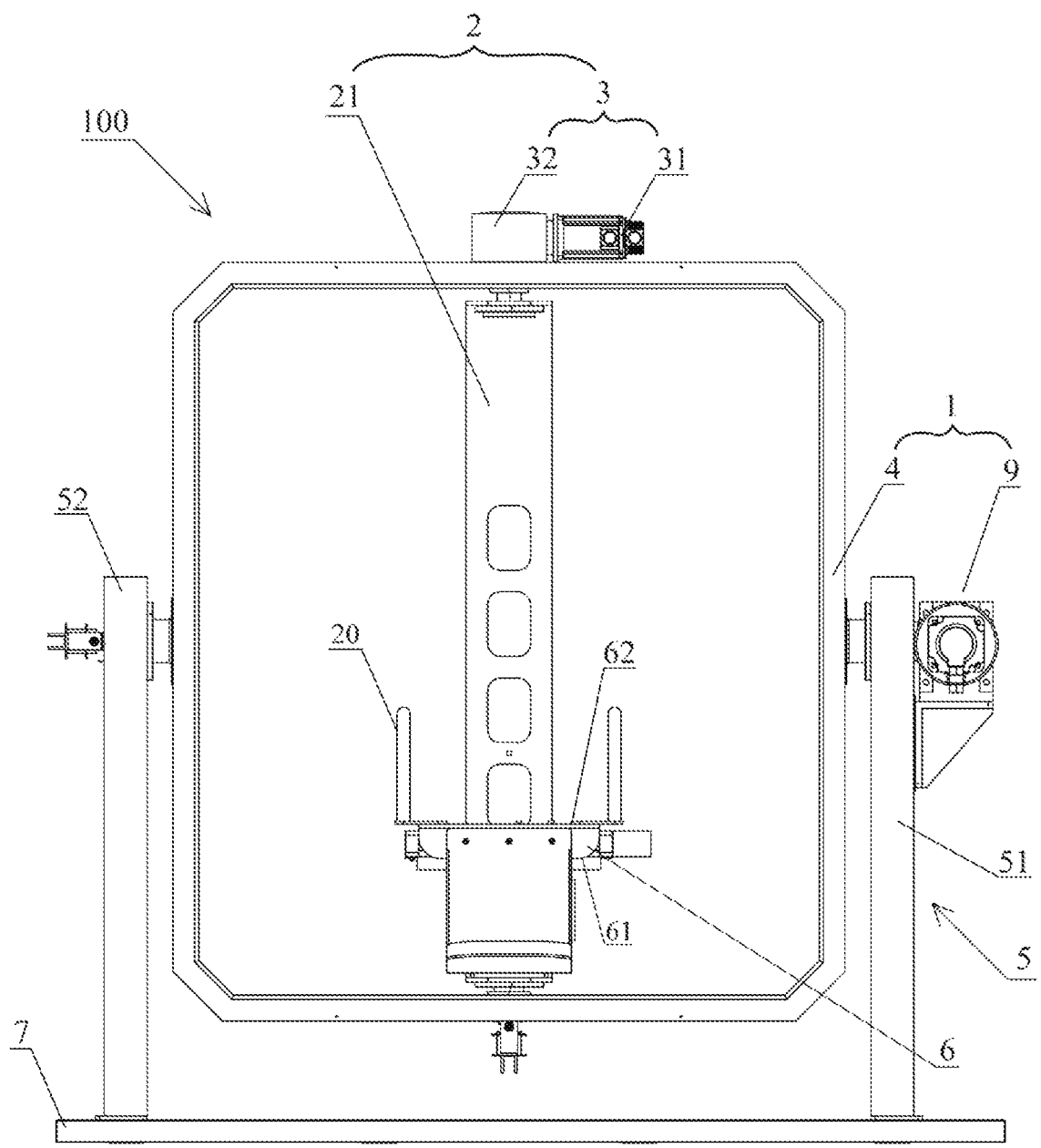
FIG. 1 is a front view of a vertigo diagnosis and treatment system according to an embodiment of the present invention.
Figure 2:
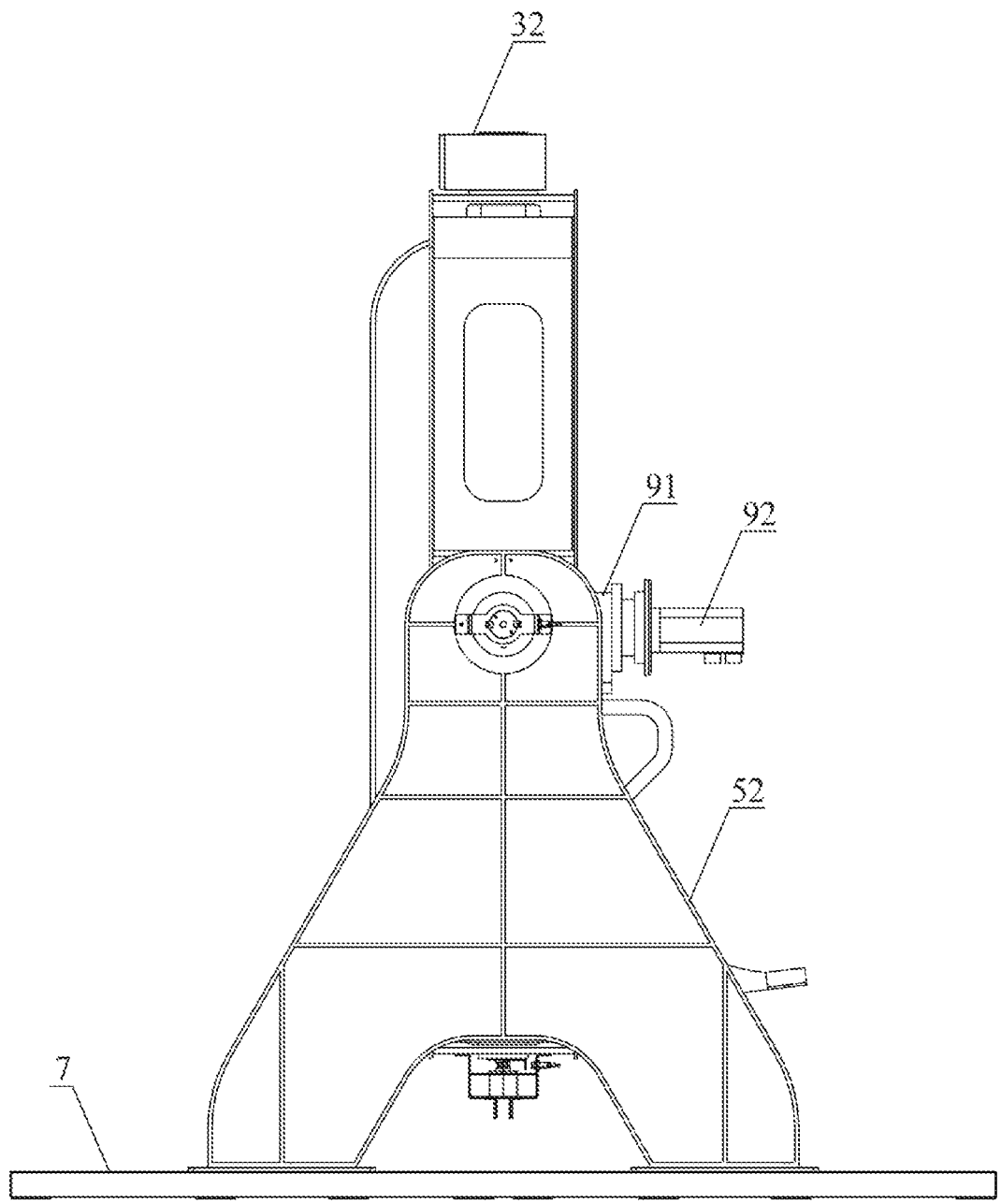
FIG. 2 is a left side view of the system shown in FIG. 1.
Figure 3:
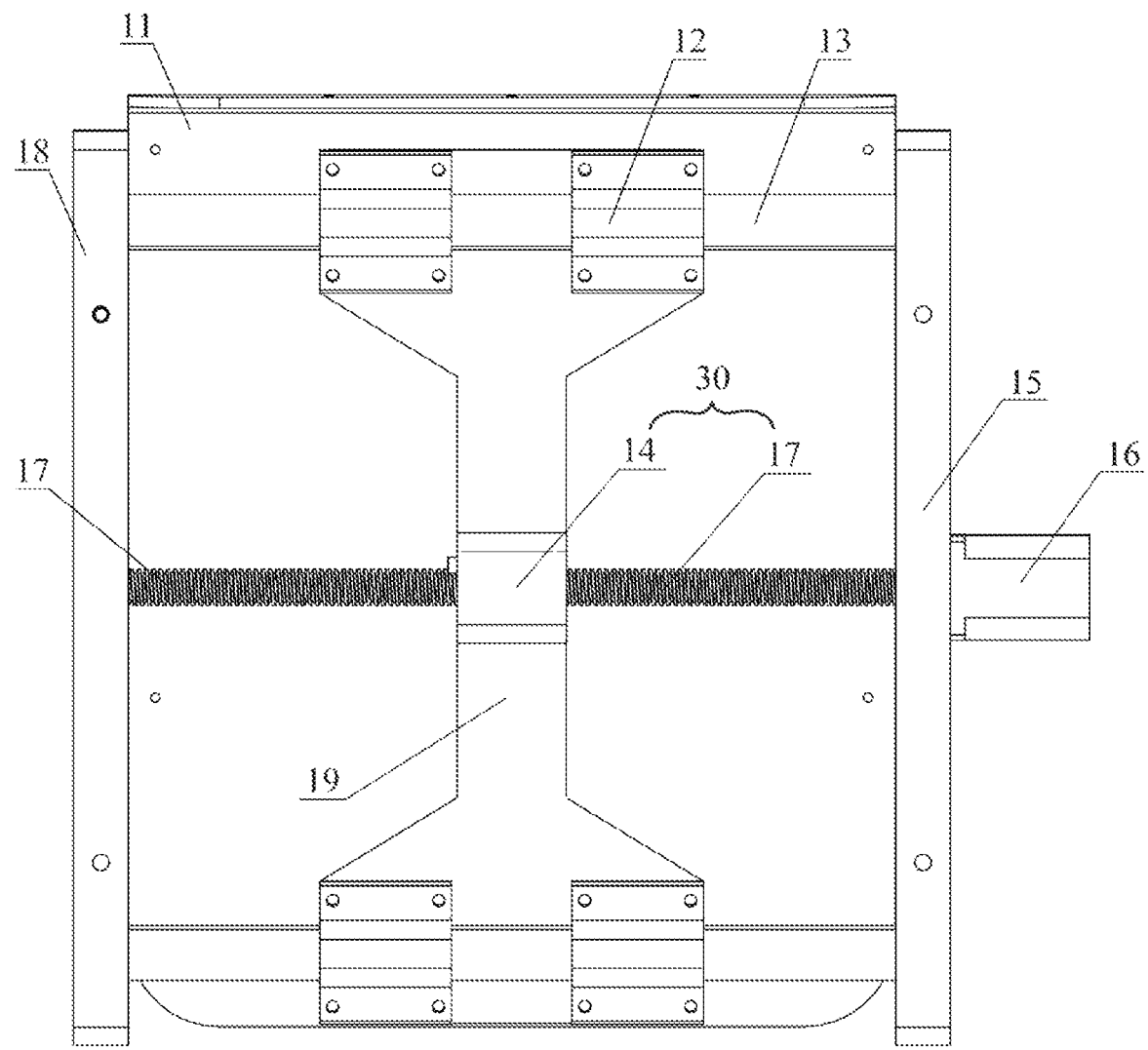
FIG. 3 is a schematic structural diagram of a seat biasing mechanism.

As shown in FIGS. 1-3, the present invention will be further described below through specific embodiments.

A vertigo diagnosis and treatment system 100 according to an embodiment of the present invention comprises a frame 5, a revolution device 1, a rotation device 2 and a seat 20. The frame 5 comprises a primary frame 51 and a secondary frame 52 arranged oppositely. The revolution device 1 comprises a power mechanism 9 and a slewing frame 4 which is arranged between the primary frame 51 and the secondary frame 52. The primary frame 51 and the secondary frame 52 provide slewing support for the slewing frame 21. The rotation device 2 comprises a power mechanism 3 and a seat rotating frame 21 on which the seat 20 is arranged. The seat rotating frame 21 is arranged inside the slewing frame 4. The slewing frame 4 provides rotation support for the seat rotating frame 21. The axis of rotation of the seat rotating frame 21 and the axis of slewing of the slewing frame 4 are perpendicular to each other.

In some embodiments, the slewing frame 4 makes a slewing motion about a horizontal axis. In this case, by arranging the fulcrum points of the slewing frame 4 on the primary frame 51 and the secondary frame 52 horizontally opposite to each other, the slewing movement of the slewing frame 4 about the horizontal axis can be realized.

In some embodiments, the slewing frame 4 is configured as a box-shaped structure, and may also be configured as an arc-shaped, elliptical, or circular structure. Box-shaped structure is preferable as it can better facilitate the setting of the seat biasing mechanism 6 and the operation of the entire equipment.

In some embodiments, the power mechanism 9 of the revolution device 1 comprises a main shaft servo motor 92 and a main reducer 91.

In some embodiments, the power mechanism 3 of the rotation device 2 comprises an auxiliary shaft servo motor 32 and an auxiliary reducer 31.

In some embodiments, the auxiliary reducer 31 is a worm gear reducer.

In some embodiments, the vertigo diagnosis and treatment system 100 includes a base 7 on which the frame 5 is fixed.

In a preferred embodiment, the vertigo diagnosis and treatment system 100 further includes a seat biasing mechanism 6 including support bases 15, 18 and a horizontal guide rail 13 arranged on the support bases. The support bases are fixed on the seat rotating frame 21. The seat 20 is slidably connected with the horizontal guide rail 13.

In some embodiments, the support bases comprise a main support base 15 and an auxiliary support base 18. A seat bottom plate 11 is arranged between the main support base 15 and the auxiliary support base 18. A horizontal guide shaft 13 is arranged on the seat bottom plate 11. A sliding block 12 is arranged on the horizontal guide shaft 13, and the seat 20 is fixed on the sliding block 12.

In some embodiments, two guide shafts are arranged on the seat bottom plate 11. Two sliding blocks 12 are arranged on each of the guide shafts 13.

In some embodiments, the seat biasing mechanism 6 is further provided with a horizontal displacement self-driving unit. The horizontal displacement self-driving unit includes a stepping motor 16, a connecting arm 19 and a power transmission mechanism 30. The connecting arm 19 fixedly connects the sliding blocks 12. The power transmission mechanism 30 transmits the action of the stepping motor 16 to the connecting arm 19.

In some embodiments, the power transmission mechanism 30 includes a T-shaped nut 14 and a T-shaped screw rod 17 which cooperate with each other. The stepping motor 16 drives the T-shaped screw rod 17 to move.

During operation, a person under test sits on the seat 20. Under the combined action of the revolution device and the rotation device, free rotation in three dimensions and hovering at any position can be achieved, so that semicircular canal VOR function detection or otolith reset treatment can be performed. Meanwhile, under the action of the seat biasing mechanism 6, a person under treatment can be shifted left and right with respect to the axis of rotation to perform a unilateral centrifugal test for detecting the functional state of the utricle-eye movement reflex.

Figure 4:
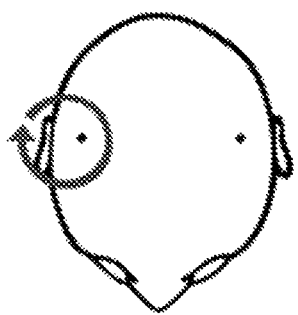
FIG. 4 is a principle diagram of a unilateral centrifugation test.
Figure 4:
Figure 4:

Specifically, embodiments of the present invention can implement the Unilateral Centrifugation Test for the otolith VOR function test. The functional status of the utricle-eye movement reflex is detected by inducing hydrodynamic changes of the endolymph of the utricle. This experiment can evaluate the function of the utricle of the otolith organs, and test the function of the left and right utricle separately. In this experiment, a person under test is first slowly rotated on the rotation axis of the horizontal semicircular canal at an acceleration of 4-6 deg/sec$^2$ until a constant speed of 300-400 deg/sec is reached. When the VOR response of the horizontal semicircular canal stops, the rotary seat is automatically translated to one side of the axis of rotation of the horizontal semicircular canal, that is, 3.5-4 cm to the left or right of the original vertical rotation axis, and continues to rotate for about 30 seconds. When the rotary seat is rotated around the axis of rotation of the right otolith, the function of the left utricle can be detected, because at this time the left utricle feels the acceleration of gravity inertia, namely a combined force of centrifugal force and gravity. Similarly, when the rotary seat is rotated about the axis of rotation of the left otolith, the function of the right utricle can be detected, as shown in FIG. 4.

The structure of the present invention is further analyzed below.

The vertigo diagnosis and treatment system 100 of the embodiments of the present invention is mainly composed of a frame 5, a main shaft rotation system (that is, a revolution device) 1, an auxiliary shaft rotation system (that is, a rotation device) 2, and a seat biasing mechanism 6. The main shaft rotation system 1 is powered by a main shaft servo motor 92, with its cantilever rotating around the horizontal axis. The auxiliary shaft rotation system 2 is powered by an auxiliary shaft servo motor 32. A seat 20 rotates around its own axis. The seat biasing mechanism 6 realizes the eccentric movement of the seat 20 at an arbitrary distance within a stroke range.

The frame 5 is mainly composed of a base 7, a primary frame 51, and a secondary frame 52. The base 7 is a supporting platform for the entire vertigo diagnosis and treatment system 100. The primary frame 51 and the secondary frame 52 provide slewing support at both ends of a slewing frame 4 to form a mechanical structure of a simply supported beam. Compared with the current cantilever beam mechanical structure of similar vertigo equipment, embodiments of the present invention can provide more stable motion support and high-speed eccentric rotation of the auxiliary shaft.

The main shaft rotation system 9 is mainly composed of a main shaft servo motor 92, a main reducer 91, and the slewing frame 4. The main shaft servo motor 92 outputs power and transmits the power to the slewing frame 4 through the main reducer 91 so that the slewing frame 4 rotates around the horizontal axis. A sudden brake can be applied for emergency, in which the main shaft servo motor 92 regenerates the brake and the main shaft rotation system 1 stops immediately. When the vertigo diagnosis and treatment system is powered off, the main shaft rotation system 1 gradually decelerates to stop, and the slewing frame 4 returns to its position under the action of gravity.

The rotation system 2 is mainly composed of an auxiliary shaft servo motor 32, an auxiliary reducer 31 (such as a worm gear reducer), and a seat rotating frame 21. The auxiliary shaft servo motor 32 conducts a decelerated transmission of power through the worm gear reducer to the rotating frame, so that the seat rotating frame 21 rotates around its axis. A sudden brake can be applied for emergency in which the auxiliary shaft servo motor 32 regenerates the brake while the auxiliary reducer 31 reversely locks itself so that the auxiliary shaft rotation system stops immediately. When the equipment is powered off, the auxiliary shaft rotation system 2 stops immediately by using the reverse self-locking of the auxiliary reducer 31.

The seat biasing mechanism 6 is mainly composed of a seat bottom plate 11, four sliding blocks 12 (e.g., a linear motion unit), two horizontal guide shafts 13, a T-shaped nut 14, a T-shaped screw rod 17, a main support base 15, an auxiliary support base 18, and a stepping motor 16. The seat 20 is mounted on the seat bottom plate 11. The slide block 12 and the horizontal guide shaft 13 provide the seat 20 with support and a degree of freedom for the left-and-right displacement in the horizontal direction. The stepping motor 16 outputs power. The T-shaped screw rod 17 conducts a decelerated transmission of power, and converts a rotary motion into a linear motion, thereby realizing the left-and-right shift of the seat 20 within a stroke range.

The above is only some embodiments of the application. It will be apparent to those skilled in the art that various modifications and improvements can be made without departing from the spirit and scope of the present application.

What is claimed is:

1. A vertigo diagnosis and treatment system, comprising a frame, a revolution device, a rotation device and a seat, the frame comprising a primary frame and a secondary frame arranged oppositely; the revolution device comprising a first power mechanism and a slewing frame, the slewing frame being arranged between the primary frame and the secondary frame and supported to slew by the primary frame and the secondary frame; the rotation device comprising a second power mechanism and a seat rotating frame, the seat being arranged on the seat rotating frame, the seat rotating frame being arranged inside and rotationally supported by the slewing frame, and a vertical axis of rotation of the seat rotating frame and a horizontal axis of slewing of the slewing frame being perpendicular to each other, wherein the system further comprises a seat biasing mechanism for driving the seat to carry out left-and-right shift with respect to the vertical axis, wherein the seat biasing mechanism comprises support bases and a horizontal guide rail arranged on the support bases, the support bases being fixed on the seat rotating frame, and the seat being slidably connected with the horizontal guide rail.

2. The vertigo diagnosis and treatment system according to claim 1, wherein the support bases comprise a main support base and an auxiliary support base, a seat bottom plate being arranged between the main support base and the auxiliary support base, a horizontal guide shaft being arranged on the seat bottom plate, a sliding block being arranged on the horizontal guide shaft, and the seat being fixed on the sliding block.

3. The vertigo diagnosis and treatment system according to claim 2, wherein two guide shafts are arranged on the seat bottom plate, two sliding blocks being arranged on each of the guide shafts.

4. The vertigo diagnosis and treatment system according to claim 3, wherein the seat biasing mechanism is further provided with a horizontal displacement self-driving unit which comprises a stepping motor, a connecting arm and a power transmission mechanism, the connecting arm fixedly connecting the sliding blocks, and the power transmission mechanism transmitting an action of the stepping motor to the connecting arm.

5. The vertigo diagnosis and treatment system according to claim 4, wherein the power transmission mechanism comprises a T-shaped nut and a T-shaped screw rod cooperating with each other, the stepping motor driving the T-shaped screw rod to move.

6. The vertigo diagnosis and treatment system according to claim 1, wherein the slewing frame makes a slewing motion around the horizontal axis.

7. The vertigo diagnosis and treatment system according to claim 1, wherein the slewing frame is configured in a shape of rectangle.

8. The vertigo diagnosis and treatment system according to claim 1, wherein the first power mechanism of the revolution device comprises a main shaft servo motor and a main reducer.

9. The vertigo diagnosis and treatment system according to claim 1, wherein the second power mechanism of the rotation device comprises an auxiliary shaft servo motor and an auxiliary reducer.

10. The vertigo diagnosis and treatment system according to claim 2, wherein the slewing frame makes a slewing motion around the horizontal axis.

11. The vertigo diagnosis and treatment system according to claim 2, wherein the slewing frame is configured in a shape of rectangle.

12. The vertigo diagnosis and treatment system according to claim 2, wherein the first power mechanism of the revolution device comprises a main shaft servo motor and a main reducer.

13. The vertigo diagnosis and treatment system according to claim 2, wherein the second power mechanism of the rotation device comprises an auxiliary shaft servo motor and an auxiliary reducer.

14. The vertigo diagnosis and treatment system according to claim 5, wherein the slewing frame makes a slewing motion around the horizontal axis.

15. The vertigo diagnosis and treatment system according to claim 5, wherein the slewing frame is configured in a shape of rectangle.

16. The vertigo diagnosis and treatment system according to claim 5, wherein the first power mechanism of the revolution device comprises a main shaft servo motor and a main reducer.

17. The vertigo diagnosis and treatment system according to claim 5, wherein the second power mechanism of the rotation device comprises an auxiliary shaft servo motor and an auxiliary reducer.

18. The vertigo diagnosis and treatment system according to claim 4, wherein the slewing frame makes a slewing motion around the horizontal axis.

19. The vertigo diagnosis and treatment system according to claim 4, wherein the slewing frame is configured in a shape of rectangle.

* * * * *